(12) United States Patent
Rehnke

(10) Patent No.: US 10,595,986 B2
(45) Date of Patent: *Mar. 24, 2020

(54) INTERNAL LONG TERM ABSORBABLE MATRIX BRASSIERE AND TISSUE ENGINEERING SCAFFOLD

(71) Applicant: Robert D. Rehnke, St. Petersburg, FL (US)

(72) Inventor: Robert D. Rehnke, St. Petersburg, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 15/918,538

(22) Filed: Mar. 12, 2018

(65) Prior Publication Data
US 2018/0206978 A1    Jul. 26, 2018

Related U.S. Application Data

(63) Continuation-in-part of application No. 14/736,945, filed on Jun. 11, 2015, now Pat. No. 9,913,711.

(60) Provisional application No. 62/010,624, filed on Jun. 11, 2014.

(51) Int. Cl.
*A61F 2/12* (2006.01)

(52) U.S. Cl.
CPC ........ *A61F 2/12* (2013.01); *A61F 2210/0004* (2013.01); *A61F 2220/0008* (2013.01); *A61F 2220/0075* (2013.01); *A61F 2230/0086* (2013.01); *A61F 2250/001* (2013.01); *A61F 2250/0067* (2013.01)

(58) Field of Classification Search
CPC ......................................................... A61F 2/12
USPC ........................................................ 623/7–8
See application file for complete search history.

(56) References Cited

U.S. PATENT DOCUMENTS

| | | | |
|---|---|---|---|
| 4,470,160 A | * | 9/1984 | Cavon .................. A61F 2/12 128/DIG. 21 |
| 6,055,989 A | | 5/2000 | Rehnke |
| 6,210,439 B1 | | 4/2001 | Firmin et al. |
| 6,548,569 B1 | | 4/2003 | Williams et al. |
| 6,867,247 B2 | | 3/2005 | Williams et al. |
| 6,875,233 B1 | * | 4/2005 | Turner .................. A61F 2/12 623/8 |
| 6,902,932 B2 | | 6/2005 | Altman et al. |
| 7,081,135 B2 | * | 7/2006 | Smith .................. A61F 2/12 606/151 |
| 7,179,883 B2 | | 2/2007 | Williams et al. |
| 7,268,205 B2 | | 9/2007 | Williams et al. |
| 7,857,829 B2 | * | 12/2010 | Kaplan ........... A61B 17/00234 606/228 |
| 7,998,152 B2 | | 8/2011 | Frank |
| 8,034,270 B2 | | 10/2011 | Martin et al. |
| 8,066,691 B2 | | 11/2011 | Khouri |

(Continued)

FOREIGN PATENT DOCUMENTS

FR    2682284    4/1993

OTHER PUBLICATIONS

Mohit P. Chhaya et al, Scientific Reports "Transformation of Breast Reconstruction via Additive Biomanufacturing", Jun. 15, 2016, 12 pgs., US.

(Continued)

*Primary Examiner* — Suzette J Gherbi

(57) ABSTRACT

An internal long term absorbable matrix brassiere including a ring member adapted to be fixed to the chest of a woman and a frusto-conical, pleated scaffold member, fixed within the ring member.

31 Claims, 13 Drawing Sheets

(56) References Cited

U.S. PATENT DOCUMENTS

| | | | |
|---|---|---|---|
| 8,425,600 B2 | 4/2013 | Maxwell | |
| 8,747,488 B2 | 6/2014 | Martin et al. | |
| 8,758,657 B2 | 6/2014 | Martin et al. | |
| 8,858,629 B2 | 10/2014 | Moses et al. | |
| 9,028,626 B2 | 5/2015 | Khouri | |
| 9,125,719 B2 | 9/2015 | Martin et al. | |
| 9,180,001 B2* | 11/2015 | Bowley | A61B 17/00491 |
| 9,326,841 B2 | 5/2016 | Martin et al. | |
| 9,333,066 B2 | 5/2016 | Martin et al. | |
| 9,480,780 B2 | 11/2016 | Martin et al. | |
| 9,498,195 B2 | 11/2016 | Schutt et al. | |
| 9,532,867 B2* | 1/2017 | Felix | B29C 48/25 |
| 9,549,812 B2* | 1/2017 | Shetty | A61F 2/0077 |
| 9,555,155 B2 | 1/2017 | Ganatra et al. | |
| 9,585,744 B2 | 3/2017 | Moses et al. | |
| 9,636,211 B2 | 5/2017 | Felix et al. | |
| 9,655,715 B2 | 5/2017 | Limem et al. | |
| 9,913,711 B2* | 3/2018 | Rehnke | A61F 2/12 |
| 9,943,393 B2 | 4/2018 | Martin et al. | |
| 9,974,644 B2 | 5/2018 | Khouri | |
| 10,028,818 B2 | 6/2018 | Felix et al. | |
| 10,058,417 B2 | 8/2018 | Limem et al. | |
| 2008/0097601 A1* | 4/2008 | Codori-Hurff | A61F 2/12 623/8 |
| 2008/0300681 A1 | 12/2008 | Rigotti et al. | |
| 2009/0125107 A1* | 5/2009 | Maxwell | A61F 2/12 623/8 |
| 2009/0234459 A1* | 9/2009 | Sporring | A61F 2/30721 623/18.11 |
| 2010/0023029 A1 | 1/2010 | Young | |
| 2010/0168808 A1* | 7/2010 | Citron | A61L 31/10 607/5 |
| 2010/0191330 A1 | 7/2010 | Lauryssen et al. | |
| 2011/0009960 A1 | 1/2011 | Altman et al. | |
| 2011/0224703 A1 | 9/2011 | Mortarino | |
| 2011/0257665 A1 | 10/2011 | Mortarino | |
| 2012/0004723 A1 | 1/2012 | Mortarino et al. | |
| 2012/0010706 A1* | 1/2012 | Schuessler | A61F 2/12 623/8 |
| 2012/0022646 A1 | 1/2012 | Mortarino et al. | |
| 2012/0029537 A1 | 2/2012 | Mortarino | |
| 2012/0150204 A1 | 6/2012 | Mortarino et al. | |
| 2012/0185041 A1 | 7/2012 | Mortarino et al. | |
| 2012/0221105 A1* | 8/2012 | Altman | A61F 2/08 623/8 |
| 2013/0006279 A1 | 1/2013 | Mortarino | |
| 2013/0103149 A1 | 4/2013 | Altman et al. | |
| 2013/0253645 A1 | 9/2013 | Kerr et al. | |
| 2013/0304098 A1 | 11/2013 | Mortarino | |
| 2014/0081076 A1* | 3/2014 | Schutt | A61B 90/02 600/31 |
| 2014/0088700 A1 | 3/2014 | Mortarino et al. | |
| 2014/0277000 A1 | 9/2014 | Mortarino et al. | |
| 2015/0112434 A1* | 4/2015 | Felix | B29C 48/25 623/8 |
| 2015/0223928 A1* | 8/2015 | Limem | A61F 2/12 623/8 |
| 2016/0022416 A1* | 1/2016 | Felix | B29C 48/25 623/8 |
| 2016/0242899 A1* | 8/2016 | Lee | A61B 17/0401 |
| 2017/0189016 A1* | 7/2017 | Gross | A61B 17/06166 |
| 2017/0196672 A1* | 7/2017 | Guterman | A61B 17/84 |
| 2017/0258574 A1 | 9/2017 | Hutmacher et al. | |
| 2017/0348090 A1* | 12/2017 | Saint | A61B 17/0401 |
| 2018/0214262 A1* | 8/2018 | Diaz | A61F 2/12 |

OTHER PUBLICATIONS

Bard Davol Inc., "Phasix Plug and Patch", product catalog, obtained from C.R. Bard, Inc. website (www. crbard.com), copyright 2013, 4 pgs., US.

Bard Davol Inc., "Phasix Plug and Patch", screenshot of C.R. Bard, Inc. website page (www.crbard.com) 2013, 1 pg., US.

Corey R. Deeken and Brent D. Matthews, "Characterization of the Mechanical Strength, Resorption Properties, and Histologic Characteristics of a Fully Absorbable Material (Poly-4-hydroxybutyrate—PHASIX Mesh) in a Porcine Model of Hernia Repair", ISRN Surgery Hindawi Publishing Corp., vol. 2013, Article Id 238067, 12 pages, Mar.-Apr. 2013.

Wayne A. Morrison et al, "Creation of a Large Adipose Tissue Construct in Humans Using a Tissue-engineering Chamber: A Step Forward in the Clinical Application of Soft Tissue Engineering", EbioMedicine 6 (2016), pp. 238-245, available online Mar. 23, 2016.

John Harman, M.D. et al, "A New Method for Partial Breast Reconstruction: 3-Year New Zealand Experience", PRS Journal, vol. 143, No. 1, pp. 49-52, Jan. 2019.

Robert D. Rehnke, M.D. (Inventor) et al, "Anatomy of the Superficial Fascia System of the Breast: A Comprehensive Theory of Breast Fascial Anatomy", PRS Journal, vol. 142, No. 5, pp. 1135-1144, Nov. 2018.

ReconSurgicalVideos on YouTube, "P4HB 3-D Solid Implant Immediate Breast Reconstruction", John Clarke, MD and Robert Rehnke, MD (Inventor), uploaded to YouTube, Feb. 20, 2016, URL: https://www.youtube.com/watch?v=swbEcrt7RTk, screen shots 0:01, 1:15, 1:30, 2:10, 8:58, 9:19.

ReconSurgicalVideos on YouTube, "MIS Mastectomy and Immediate Reconstruction with P4HB Scaffold and Fat Grafting", Dr. Robert Rehnke (Inventor), uploaded to YouTube, Mar. 25, 2016, URL: https://www.youtube.com/watch?v=4QzYsFAA7Jc, screen shots 0:07, 4:52, 6:22, 9:38, 10:03, 11:18, 11:42, 11:58, 12:24.

ReconSurgicalVideos on YouTube, "Organic Breast Reconstruction with Autologous Fat Graft, Biodegradable Scaffold", Dr. Robert Rehnke (Inventor), uploaded to YouTube, Mar. 28, 2017, URL: https://www.youtube.com/watch?v=MyzhDBQNneA, screen shots 0:01, 0:05, 5:56, 6:06.

ReconSurgicalVideos on YouTube, "Immediate Breast Reconstruction Without Implants, Skin and Nipple Sparing Mastectomy, Internal Mastopexy Purse String", Dr. Robert D. Rehnke (Inventor) and Dr. John Clarke, uploaded to YouTube Apr. 9, 2017, URL: https://www.youtube.com/watch?v=dR_IXLygxi8, screenshots 0:02, 0:05, 0:24, 0:35, 1:34, 2:57, 3:12, 3:29, 3:47, 4:11, 4:29.

Roger K. Khouri, M.D. et al, "Megavolume Autologous Fat Transfer: Part I. Theory and Principles", PRS Journal, vol. 133, No. 3, Mar. 2014, pp. 550-557.

* cited by examiner

INTERNAL LONG TERM ABSORBABLE MATRIX BRASSIERE AND TISSUE ENGINEERING SCAFFOLD

CROSS-REFERENCE TO RELATED PATENT APPLICATION

This application claims priority from pending U.S. patent application Ser. No. 14/736,945 filed Jun. 11, 2015, which claims priority from U.S. provisional patent application Ser. No. 62/010,624 filed Jun. 11, 2014, the entire disclosures of which are incorporated herein by reference.

BACKGROUND OF THE INVENTION

Field of the Invention the present invention pertains generally to a device for surgical enhancement of the breast by enlargement and/or correction and prevention of breast ptosis and acts as an internal long term absorbable matrix brassiere. More particularly, the present invention constitutes a device, made of long term absorbable matrices, that repairs, enhances and/or reinforces bodily tissue internally, such as the breast, for example and, in the case of the breast, is responsible for the shape and anchoring to the chest wall via the circum-mammary ligament.

Brief Discussion of the Related Art

Brassieres had their origin in the 19th century and were preceded by the corset, which was fabricated in one piece with ribbing as supports, originally made of whalebone then metal, to push the breast up and squeeze the waistline in. The origins of similar articles of fashion dates back 3,000 years to the Minoan civilization, whose Snake Goddess wore a corset like device which pushed the breasts up and together, exposing them in an uncovered central position. The succeeding Mycenaeans continued the tradition, as the breast held special cultural and religious significance to them. These undergarments have always had roots dually in fashion and the more practical supportive health concerns. They have been an expression of female beauty and social hierarchy.

One hundred years ago, Mary Phelps Jacob (after marriage known as Caresse Crosby), obtained a patent from the US patent office for a backless brassiere she made from two handkerchiefs. Legend has it that Mary, who was 19 year old member of New York City society, had to create an alternative to a corset when planning her ensemble for the debutant ball. She and her maid attached two handkerchiefs together with pink ribbon and a cord. The fashion was such a success that her friends commissioned more made for themselves. Realizing she had invented something useful, Mary went on to submit a patent for a "Backless Brassier", which was granted in November of 1914. Years later she would sell this intellectual property to Wamers Brothers Corset Company, of Bridgeport, Conn. There are many treatments for omen who have undergone mastectomies due to cancer. Such treatments all have some form of prostheses that fill the cup of the bra on the effected side.

Plastic surgery figured prominently in the story of youthful, full, and lifted breast, when the breast implant was introduced in the 1960s. Thomas Cronin and Frank Gerow collaborated with Dow Corning in 1961 to develop the first silicone breast implant. Shortly after, in 1962 the first breast augmentation with a silicone implant was performed. The rest, as they say, is history, over 300,000 breast implant surgeries are performed each year.

The anatomy of the breast and chest has a great deal to do with the shape and perkiness of the breast, something both bras and implants are trying to influence. The breast, an organ consisting of both glandular tissue and fat, is shaped by collagen connective tissue, called fascia that anchors and supports the breast to the underlying chest wall. Sir Astly Cooper, in the 19th century, described the two layers of superficial fascia that surround the breast and anchor it to the chest wall. He described the connective tissue extensions, named after him (Cooper's ligaments) which run from this superficial fascia up to the under surface of the skin to anchor the skin to the breast. It has been felt that when Coopers ligaments stretch out, the breasts then sag. However, what has not been appreciated until now istle exact nature of how the superficial fascia attaches to the chest—the circum-mammary ligament. This fascia, like a corral, is called the circum-mammary ligament, which defines the perimeter of the breast. In addition, it fuses to the fascia covering the chest wall and anchors it in place. The most defined aspect of this structure is located under the breast, called the infra-mammary fold ligament. The next most developed is the medial, or inner aspect of the corral. This inner portion of the circum-mammary ligament causes the separation between the breasts and is responsible for the cleavage. Laterally, towards the outer portion of the breast, the circum-mammary ligament is not as strong or well defined. It is this portion of the suspensory ligament of the breast that is most responsible for sagging, or ptosis, of the breast. As was previously mentioned, the breast sits upon the chest wall which is its foundation. The foundation has a great deal of impact on the shape and projection of the breast. Most human anatomy is not perfectly geometric or symmetric. Thus, there are usually differences in the boney rib cage on the left and right that lead to asymmetry of the breasts. With a person lying do their back, or as anatomists say the supine position, the rib cage is like a flattened cylinder—that is wider than it is tall. Also, as one travels from the center point of the chest, or sternum, towards the outer or lateral aspect, the flat portion of the chest must slope downward. As one moves out from the center and around the chest, it becomes more cylindrical as it turns to the back, which once again is flattened. The portion of the breast located on the downward slope of the lateral chest wall, effects how it is pulled down by gravity in the supine position or pressed away from the center of the chest in the prone position (like the keel of a boat pushing through water). So, it is true that gravity pulls the breast down, but this happens because the inherent anatomy (weaker attachment of the circum-mammary ligament to the chest and a sloping chest wall laterally) and its effect in the prone and supine position. A flatter, more rectangular chest supports the breast position more than a more rounded, cylindrical chest which leaves the breast attached to the side of the chest without an underlying foundation. Since the human form is asymmetric, one can have less support from the chest on one side, than on the other, resulting in more sagging, or ptosis, on that side. The larger the breast the more the etching force The presence of breast implants can greatly exacerbate this situation.

Ironically, plastic surgery involving breast implants frequently weakens the body's natural, internal bra—the superficial fascia system and circum-mammary ligament. Even more destructive to the shape of the breast is mastectomy for breast cancer. Despite modern skin and nipple sparing procedures having been accepted as cutting-edge cancer care, most surgeons ere insufficiently knowledgeable or skilled to save the circum-mammary ligament and take full advantage of this minimally invasive approach to mastectomy.

Therefore many woman, with large heavy breasts or women who have had breast surgery, end up with weakened supporting structures of the breast and suffer breast sagging. The original breast lift and reduction technique was developed by plastic surgeon Robert J. Wise. It used a "key hole" skin reduction pattern that left an anchor shaped scar on the breast. A technique which followed, by LeJour, omitted the horizontal scar in the infra-mammary fold and is referred to as the "lollipop" scar. In the 1990s a minimal scar technique developed by French plastic surgeon named Binelli was popularized to correct breast sagging as a primary mastopexy or in conjunction with a breast implant. This approach did not use large skin reductions, as in previous techniques, but limited scars to the peri-areolar border and used internal sutures to shape the breast gland. A plastic surgeon in South America, Goes, was even more innovative and added the use of synthetic permanent mesh fabrics, placed between the skin and breast gland, to shape the breast in a manner consistent with an internal bra. Because these permanent implants were too frequently palpable or resulted in complications related to the mesh (infection, erosion, chronic pain) most American doctors did not adopt these imaginative techniques.

In recent years, tissue a were d to treat these problems. In situations where breast implants or mastectomy surgery had broken down the natural support structures of the lateral, inferior or medial boundaries, a cadaver or animal skin graft, known as acellular dermis, was used to repair the stretched out tissues. In 2010, as an alternative to tissue grafts, Novus Scientific introduced the first long term absorbable synthetic matrix for repair and support of weak or damaged body tissues. Since, three other large medical manufacturers have introduced similar products. But still they all have been used a substitutes for tissue grafts (that are two dimensional sheets) like their acellular dermal predicates.

U.S. Pat. No. 6,055,989 to Rehnke deals with the principle of fascial clefts. Fascial clefts are potential anatomic spaces between layers of known fascia in the body which are fused together at anatomic boundaries. Because the fascia is thin and transparent, like Saran wrap, it can be invisible to those not skilled in the art. However, once one is aware of its presence, its effects can be appreciated and used to great surgical advantage. In the region of the breast, knowledge of the superficial and deep fascial relationships is crucial to all surgeries on this organ. The '989 patent teaches the use of blunt, balloon dissection of the fascial cleft below the b react known as the "sub-glandular space." It was found that the sub-glandular fascial cleft could be opened by balloon dissectors, which could dissect until they reached the peripheral borders of the breast, as defined by the circum-mammary ligament.

The breast is an organ of ectodermal origin, whose cells penetrate the mesoderm and organize into a network of lobular milk producing cells which are connected to the nipple through milk ducts, lined by ductal cells. These breast tissue cells, of ectodermal origin, are surrounded by mesenchymal fat cells, and contained within a dense connective tissue capsule making up what is known as the "corpus mammae." (The corpus name what must be removed during mastectomy for breast cancer.) The corpus mammae is sandwiched between the two layers of superficial fascia and a surrounding insulating layer of fat. Deep to this sandwich, and just on top of the deep fascia of the pectoralis major, is the fascial cleft known as the sub-glandular space. The two layers of superficial fascia that surround the breast fuse to each other and the deep fascia in circle around the breast, defining its boundaries and shaping its form; it is known the "cir-cum-mammary, or circum-mammary or circumferential mammary ligament."The decusating and intermingling fibers of the superficial fascia and deep fascia fibers are mixed with varying amounts of fat, depending on the percent body fat of the patient and the particular aspect of the circum-mammary ligament. For instance, it is thickest and most defined at the inferior border at the fifth costal interspace, or "infra-mammary fold." The medial aspect of this lazy circular border is the reason for the cleavage point between the breast and is well defined but not thick and fatty. The lateral aspect is less well defined but wide, much more elastic than the inferior or medial boundaries, and located just anterior to the anterior axillary line. Superiorly, the cir-cum-mammary ligament is at its thinnest and hardest to appreciate, in comparison to the infra-clavicular region. A useful plane of surgical dissection is located within the deep layer of fat, deep to the corpus mammae and within the deep layer of superficial fascia—the so called "intra-fascial" dissection plane. This plane of dissection preserves the integrity of the superficial fascia system and gives exposure to the circum-mammary ligament.

U.S. Published Patent Application No. 2008/0300681 to Rigott et al indicates that if a tissue expander device is placed within layers of tissue in the human anatomy and gradually exerts tensile stress on the tissue, it will induce biologic tissue growth in e desired fashion. Furthermore it teaches the injection of fat, stem cells (and other progenitor cell) growth factors and pharmaceuticals into the tissue layer experiencing tensile stress. It recapitulates the teachings of the Rehnke '989 patent in regard to the fascial cleft anatomy of the breast and its natural boundary, the circumferential mammary ligament Rigott states that, "it has been found that these defined layers also offer a region for tissue growth as disclosed herein."

U.S. Published Patent Application No. 2012/0221105 to Altman et al relates to an implantable device for use in tissue and ligament repair. The device is comprised of knitted, slowly absorbable silk fibers with a continuous fiber traversing it. The preferred embodiment involves its use as a sheet of fabric, or mesh, that is used in place of Il lar dermal cadaver grafts in the performance of breast reconstructions and all manner of cosmetic breast surgeries and mention that a scaffold can be used, as an internal scaffold to act as a bra to immediately support a geometrically complex implantation site at the time of surgery which would ideally provide the body both time and structure necessary for optimal healing. Simple sheets of two-dimensional matrix are used to reinforce various regions of the breast depending on the need of each finical case. The device shown as a sheet of fabric, is simply folded over to reinforce regions of the breast borders, such as infra-mammary fold, medial cleavage, or lateral border. Known surgical procedures and maneuvers that have been a part of plastic surgery of the breast for ten years are used with the substitution of the absorbable silk synthetic material for the traditional acellular dermis product.

U.S. Pat. No. 7,998,152 B2 to Frank shows an implantable device made for use in a pen-areolar mastopexy, which allows s for a transfer of shaping tensions to the device, as opposed to simply on to the permanent purse string used in per-areolar mastopexy. The device is annular or frusto-conical in configuration and can be constructed of absorbable material or acellular tissue graft. The truncated, cone shaped device may have a series of teeth extending out from the surface that engages the breast gland, and thus holds it in the more desirable projecting, state seen in youthful breasts. It is designed to be placed through the peri-areolar incision, under the skin and on the superficial surface of the breast gland. It allows for use of an absorbable peri-areolar suture, that tightens the skin envelop around the areola. The device addresses only the skin envelope relaxation, seen in breast ptosis; it does not address the more important causation of breast sagging, the enlargement and stretching out of the circum-mammary ligament.

Professors Jain Farhadi and Kefah Mokbel have performed a surgical procedure at Guy's Hospital in London, making use of an implantable device developed in 2007, wherein a synthetic bra made of a silicone cup is placed between the skin and the lower pole ref the breast; it is anchored to the rib cage with silk straps.

The previously mentioned prior art devices do not describe a pre-fabricated internal bra, designed for surgical use, to prevent the relaxation of the fascial shaping structures of the breast that hold it, and when applicable also hold breast implants, in their youthful position on the chest. Therefore, it can be appreciated that there exists a continuing reed for a new and improved pre-fabricated long term absorbable matrix device, designed for surgical creation of an internal bra that mimics and strengthens the circum-mammary ligament.

SUMMARY OF THE INVENTION

The present invention overcomes the above described disadvantages of the prior art by preventing breast sagging, or ptosis, which comes from the stretching out of the superficial fascial system (circum-mammary ligament or CML) that shapes and conforms the breast its natural position on the chest wall. The breast itself as no shape apart from the superficial fascia system. The circum-mammary ligament establishes the position on the chest wall and pushes the volume of the breast into a projecting vector as the diameter of this ring of fascia gets smaller. The anterior and posterior lamella of the superficial fascia control the projection and thus shape the breast. Ptosis is a result of both the diameter of the circum-mammary ligament enlarging, and the anterior/posterior lamella of the superficial fascia relaxing. The loss of support allows the skin of the breast to stretch as result. Factors such as genetic inheritance (strength of skin and connective tissue), amount of body fat, history of weight gain and loss, number of pregnancies, breast feeding, and shape and contour of the chest wall, are the contributing factors that determine a woman's natural breast shape. The typical order of things is that women develop breasts at puberty and are "perky", followed by enlarged breast volume during child bearing years, at which time they develop a pleasant tear drop fullness; they involute or deflate after child bearing, at which time they then sag or, in medical terms, become ptotic. In the modern era, women have resisted this natural order of things (the "National Geographic" condition of the breast). Many modern women have sought help through plastic surgery, taking advantage of breast reduction, breast lifts and/or breast implants to correct these changes and preserve a more youthful breast.

The present invention is a device, when used for the breast, in the form of n internal brassiere device, made of long term, absorbable materials. The device is three-dimensionally shaped to mimic the breasts own fascial system of support, the circum-mammary ligament. The device includes a ring member forming a circular base on the chest, which is placed on top of the deep fascia of the pectoralis major, or just superficial to it, within the posterior superficial fascia.

The first component or ring member of the device of the present invention can be a circular three-dimensional tube made of long term absorbable fibers. The ring member can also include fibers comprised of a non-absorbable material, such as polypropylene. A non-absorbable suture is located within the tube. The ring member can be inserted in a large diameter condition and, once anchored to the circum-mammary ligament, cinched into a smaller diameter by pulling the internal suture tight and tying it The ring member can have a pleated, gathered nature, like an accordion, which allows it to have a variable diameter. It is designed to be placed in the plane below the corpus mammae and within the posterior lamina fascia—the so called "intra-fascial" dissection plane. In one embodiment, the ring member is formed by a twine, barbed suture, made of part long term absorbable and part non-absorbable twines and the suture is placed through the circum-mammary ligament and pulls it to a smaller diameter once it is placed and tied. The suture combines the function of the first component ring member and the internal anchoring suture that runs ,as purse string throughout the circum-mammary ligament. The first component suture is thicker than traditional sutures and can be 3 to 5 millimeters in width. It is a multi-filamented suture, with both absorbable and non-absorbable filaments. Some of these filaments radiate off of the central core with directional extensions which allow the device to be pulled through the tissue of the circum-mammary ligament in one forward direction but would grab the collagen fibers and prevent movement of the suture in a backward direction The twine filaments radiate out from the central core or the ring member in a helical manner and, thus, provide firm anchorage to the tissue of the circum-mammary ligament. In another embodiment, the twine ring/suture is inserted in the tissue using a circular suture passer, attached to a hand piece. The suture passer is fashioned so as to allow it through the circumference of the circum-mammary ligament in four to five suture passes. This embodiment allows for placement of the ring member and anchoring suture in one step. The suture passer allows the placement, within the circum-mammary ligament, in a faster and easier fashion Once the ring member is positioned, the surgeon sutures the ring member to the circum-mammary ligament. This is accomplished with interrupted, non-absorbable sutures that are placed along the entire circumference of the circum-mammary ligament.

In another embodiment, there is no permanent suture within the ring member. The ring member is attached to the circum-mammary ligament with non-absorbable running suture that courses in and out of the ligament and ring member in such a fashion as to pull both the circum-mammary ligament and mg member into a member diameter when the suture is pulled taut and tied. In yet another embodiment, the ring member is more like a partially absorbable suture or twine having spirally oriented fibers or filaments emanating from the central core thereof to permit advancement through the circum-mammary ligament fibers in the forward direction but resist sliding backward. The large suture ring member is on the order of 5 millimeters in diameter. It not only narrows the diameter of the breast base immediately at the time of surgery but provides an anchor of healing tissue that integrates the collagen of the circum-mammary ligament with the healing ring of the first member.

The second member or cup member functions like the "cup" of a traditional bra and is attached, with non-absorbable sutures, to the ring member after it is secured and tightened. It is a three-dimensional, frusto-conical shaped structure, which is composed of one or more long term absorbable fibers forming knitted sheets of mesh material that are folded and pleated and maximize surface area in a given volume. It can have a small percentage of the knitted fibers composed of permanent material, such as polypropylene The base of the frusto-conical structure is placed within the ring member and is anchored to it with sutures. The cup member pushes the breast tissue up and out and, therefore, gives the breast more projection away from the plane of the chest wall. It also acts as a scaffold for patient tissue ingrowth and as a surface that fat grafting can be placed on, along with other tissue engineering substances, such as platelet gel, various growth factors, adipose extra-cellular matrix antibiotics, anti-cancer drugs, and other chemicals and/or proteins which help direct the engineering of desired new tissue. The pleated or folded material of the cup member forms semi-open compartments or pockets arranged radially around a central core. The cup member is designed as a fully, long term absorbable component in some embodiments, but can contain a small percentage of non-absorbable fibers in other embodiments. It is a three-dimensional matrix which allows for arterial and tissue ingrowth and can be used to engineer a fuller more projecting breast when autologous fat transplantation is injected into its inter tires. Accordingly, the need for a traditional breast plant can be avoided. If desired another engineering scaffold can be used for small to medium autologous augmentation, or in place of a silicone implant, in cases of breast reconstruction following mastectomy. In the special case of mastectomy for breast cancer, or prophylactic mastectomy, the frusto-conical tissue engineering scaffold acts as a stent within the mastectomy defect and prevents collapse and contracture of the wound thus allowing space for fat grafting into and around the device to restore a whole breast.

The internal brassiere device can incorporate a third member or anchoring component composed of twined, barbed suture passing from the frusto-conical cup member through the substance of the corpus mammae and breast. Emanating from the central core of the frusta-conical member, are twine sutures that pierce through the corpus mammae and then penetrate the skin of the breast at strategic locations, roughly, at the central nipple, 12, 2, 4, 6, 8, and 10 o'clock. These sutures are anchored in the cup member and placed through the breast gland, so as to exit the skin. They are held under tension while the scissors push down on the skin and cut the suture. This maneuver insures the suture will recoil below the subcutaneous fat and stay within the anterior lamella fat. This maintains the desired relationship between a larger breast gland and the device, anchored to the chest wall and, thus, prevents downward shifting of the breast away from the desired location on the chest. In this manner, breast ptosis is prevented.

Accordingly, the present invention provides a long term absorbable internal brassiere device, whose shape and engineering is dictated by the breast's natural superficial fascial anatomy—the circum-mammary ligament. The present invention takes into account that a major contributor to breast ptosis is the stretching out of the circum-mammary ligament when a heavy breast o breast implant slides down off the inclined chest wall, while a person is in a supine or prone position. The design of the internal brassiere device makes use of two or three members or components which, assembled together, form the internal brassiere device. The first member is a ring member with an internal purse string, which is designed to b placed in the intra-fascial plane adjacent the cirum-mammary ligament. The ring member anchored to the circum-mammary ligament with permanent interrupted sutures. When the purse string is pulled tight and tied, the base foot print of the breast is narrowed and thus gathers the breast together and adds to its projection.

The second member has a cup-like shape, is located within the first member and is placed deep in the corpus mammae within the posterior layer of fat and within the deepest layer of superficial fascia. In cases of breast reconstruction, the second member is placed below the skin and anterior fat layer that covers the corpus mammae. When a breast implant is called for, the second member scaffold can be used instead of a traditional saline or silicone implant. The third member is the anchoring component formed by the tissue sutures. The present invention is particularly advantageous for women who have had plastic surgical enhancement of the breast (with breast implants or fat grafting), mastopexy, breast reduction, or immediate breast reconstruction following mastectomy for breast cancer. Additionally, the internal brassiere device of the present invention provides effective support and shaping for women with breast implants who desire that the implants be removed. The internal, long term absorbable matrix brassiere according to the present invention provides a synthetic internal brassiere that mimics the principal structure of nature's superficial fascial bra, the circum-mammary ligament. Tightening the circum-mammary ligament narrows the breast base diameter and projects the breast, the way an underwire bra does. The frusto-conical scaffold creates more volume and projection the way a push up, or padded bra does.

The present invention can be provided as a pre-fabricated internal bra, designed for surgical use, to prevent the relaxation of the fascial shaping structures of the breast that hold it and, when applicable, augment the volume of the breast. The internal brassiere device avoids the negative aspects of traditional breast implants that stretch out end weaken the superficial fascia system of the breast.

Another feature of the present invention is that an improved pre-fabricated long term absorbable matrix brassiere device according to the present invention provides for surgical creation of an internal bra that mimics and strengthens the circum-mammary ligament.

The internal brassiere device of the present invention has the advantage of mimicking the anatomical structure of the superficial fascia system of the breast and provides a device useful to surgically restore the correct tensional integrity of a youthful breast.

Other aspects and advantages of the present invention will become apparent from the following description of the invention taken in conjunction with the accompanying drawings wherein like parts in each of the several figures are identified by the same reference characters.

BRIEF DESCRIPTION OF THE DRAWINGS

FIG. 6 illustrates the problem that exists when a woman with sizable breasts sleeps in a recumbent horizontal position.

DETAILED DESCRIPTION OF THE INVENTION

Figure 1A:
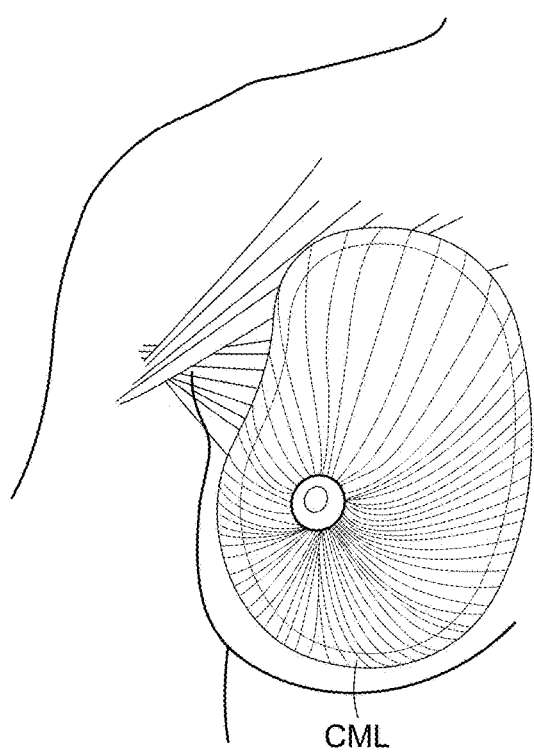
FIGS. 1A and 1B show the circum-mammary ligament surrounding the breast and being weaker laterally, FIG. 1B including an enlarged sectional portion of the breast.
Figure 1B:
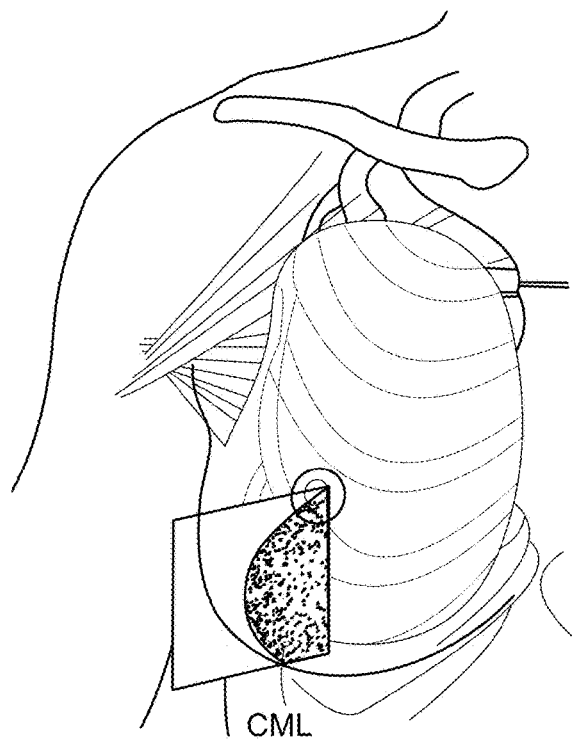
Figure 2:
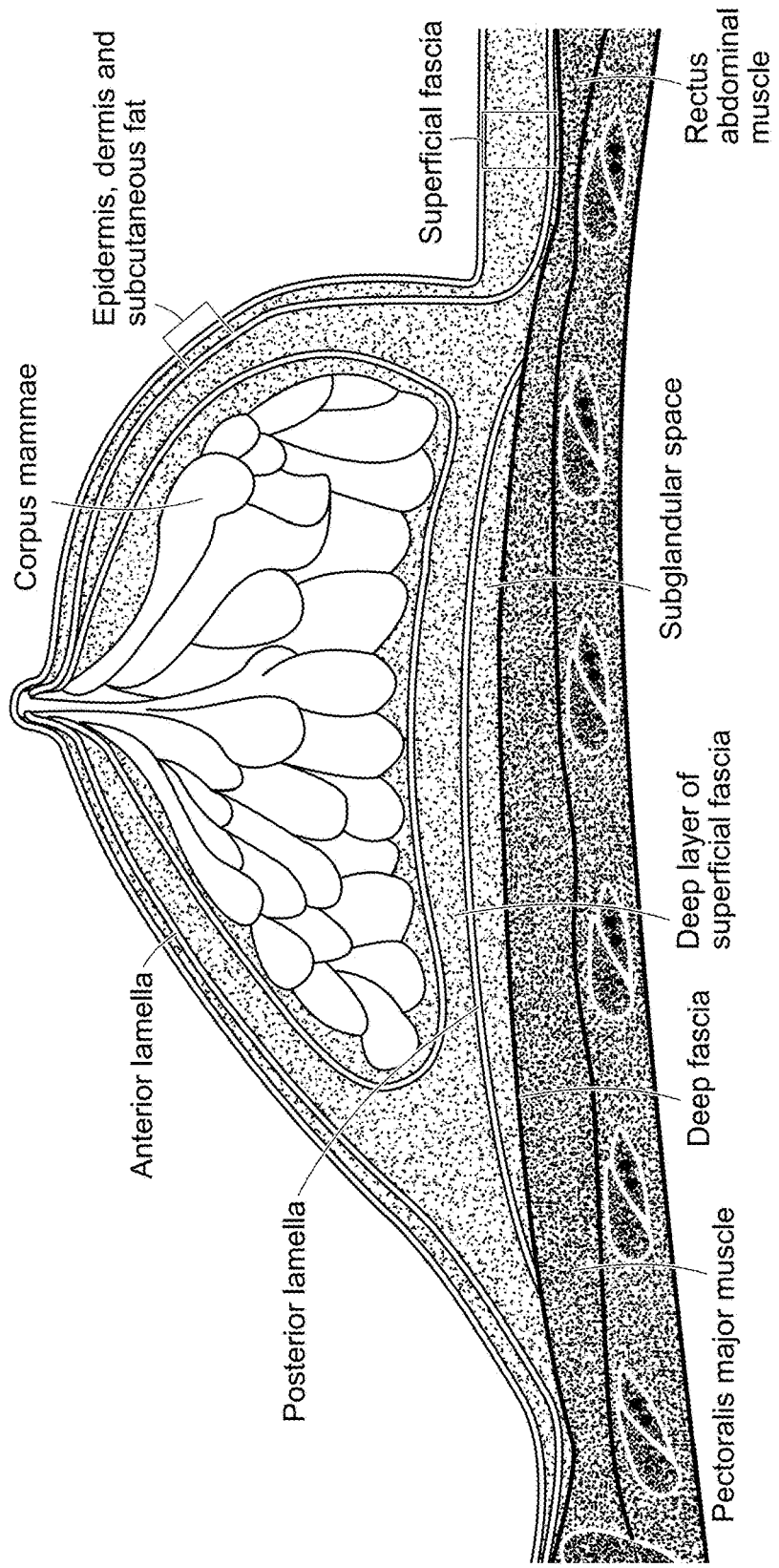
FIG. 2 is a sectional sagittal view of the superficial fascia system of the breast.
Figure 3:
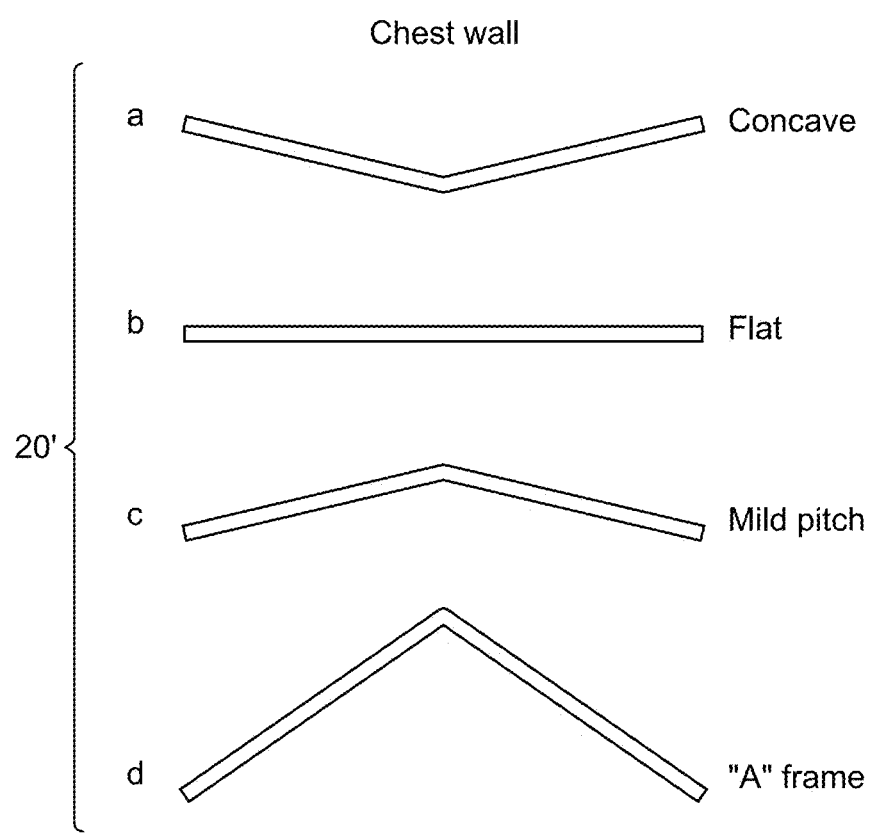
FIG. 3 shows the various slopes in the human chest wall with a person in the supine position and illustrates the great deal of variation seen in the "topography" of the chest wall from one person to another, and from side to side in the same person, and also illustrates that asymmetry in human anatomy is the rule, not the exception such that a person could have a flat right side of the chest, and a sloped pitch to the left side.
Figure 4:
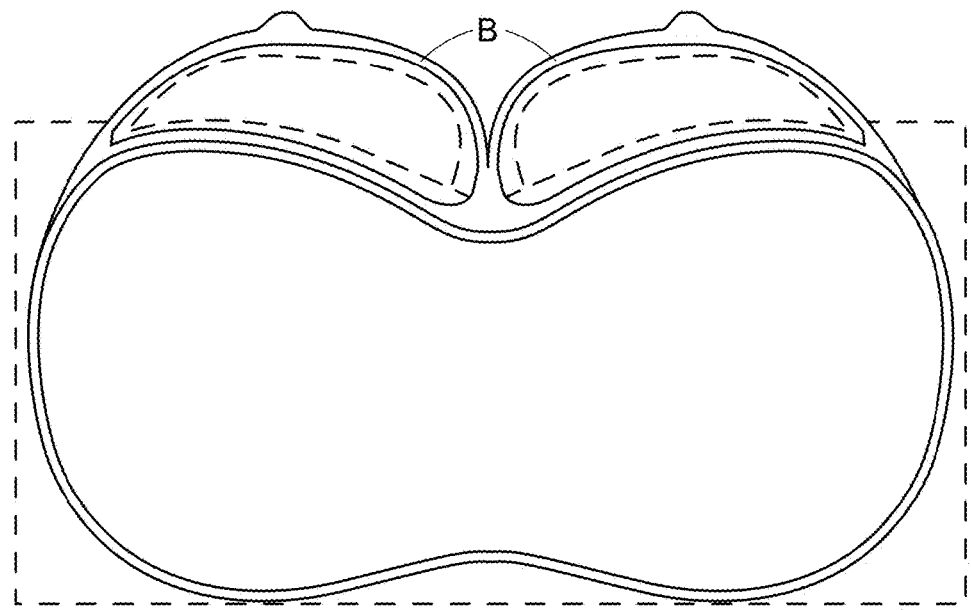
FIGS. 4, 5 and 6 illustrate a sunken central chest, or pectus excavatum, a rectangular shape chest, or flat chest, which gives the best support for the breast and implants when present and when the pitch of the chest wall begins to progressively become more sloped, and lateral movement of the breast, respectively.
Figure 5:
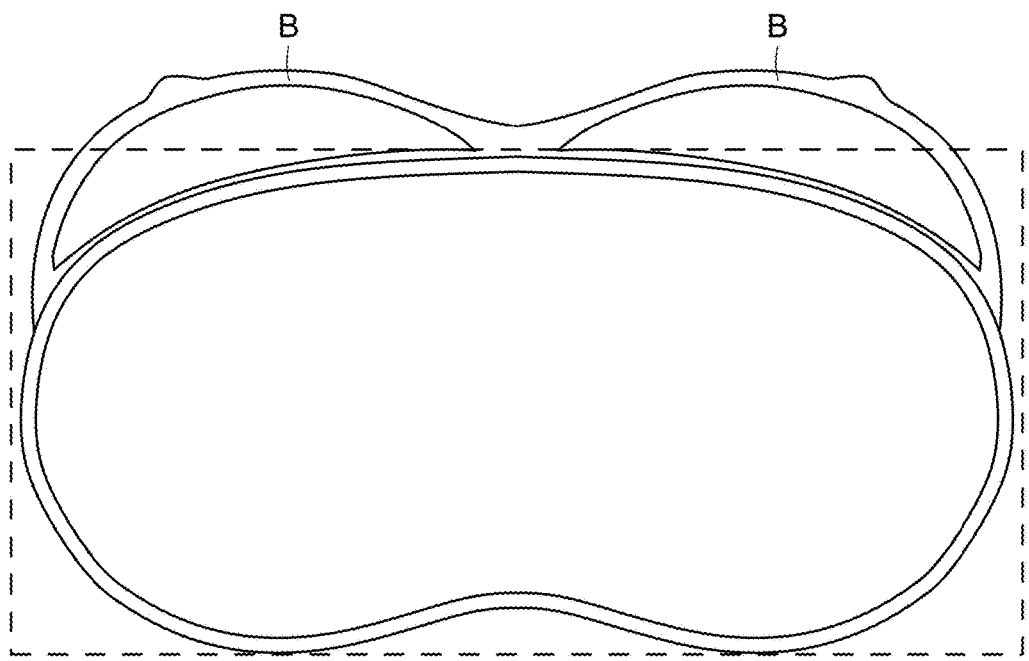
Figure 6:
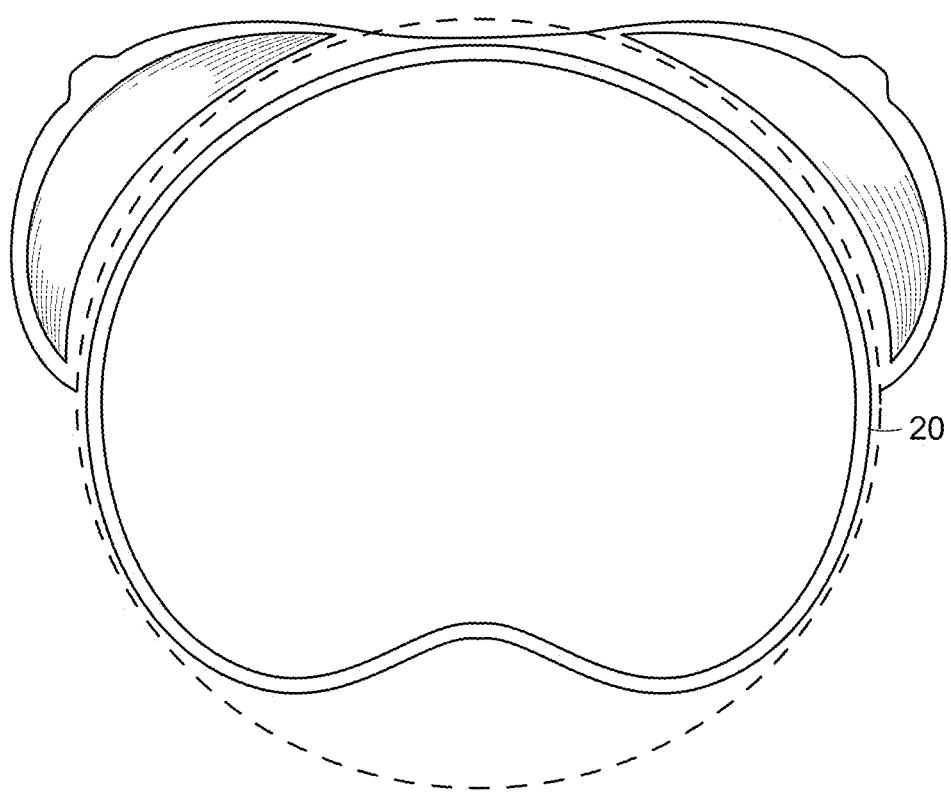

The chest wall 20 generally slopes downward as one moves from the center, or sternal area, towards the lateral chest wall. The various configurations exist as a result of the basic patterns 20' seen in FIG. 3 and the fact that there is propensity for asymmetry in the human body, largely because of asymmetry of the underlying skeleton. The breast B tends to follow the contour of the chest wall, with unusually close cleavage in conditions like those seen in FIG. 4. This condition is known as pectus excavatum. The chest configuration that is most desirable for maintaining youthful perky breast, or keeping a desirable position of the breast following plastic surgery, is the rectangular shape seen in FIG. 5. In this situation there exists a stable, horizontal support for the mass of the breast, with or without a breast implant. During the roughly eight hours per day that a person sleeps they are n either the supine or prone position at least half of the time. This rectangular configuration protects the circummammary ligament from stretching out by supporting the breast in the horizontal position. The worst condition of the chest for maintaining a youthful, perky breast is that seen in FIG. 6—the round or cylindrical chest 20. In this state, the breasts ere basically cantilevered off of the chest well without any support.

Figure 7A:
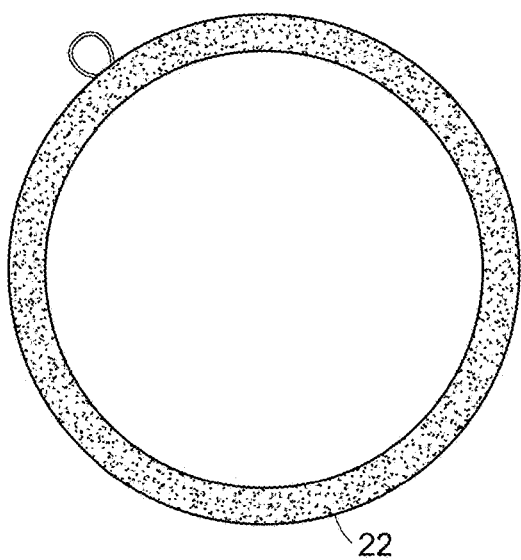
FIGS. 7a and 7b show plan views ring member of the internal device according to the present invention in pre-cinched and cinched shapes, respectively.
Figure 7B:
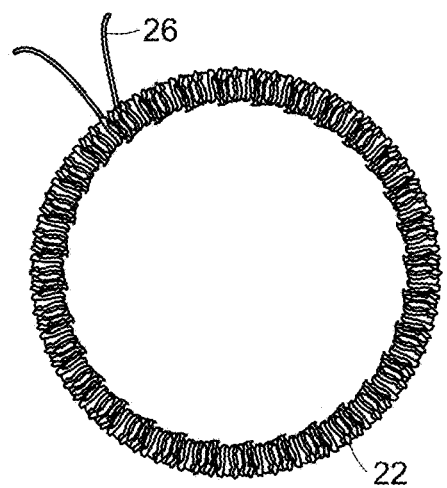
Figure 8:
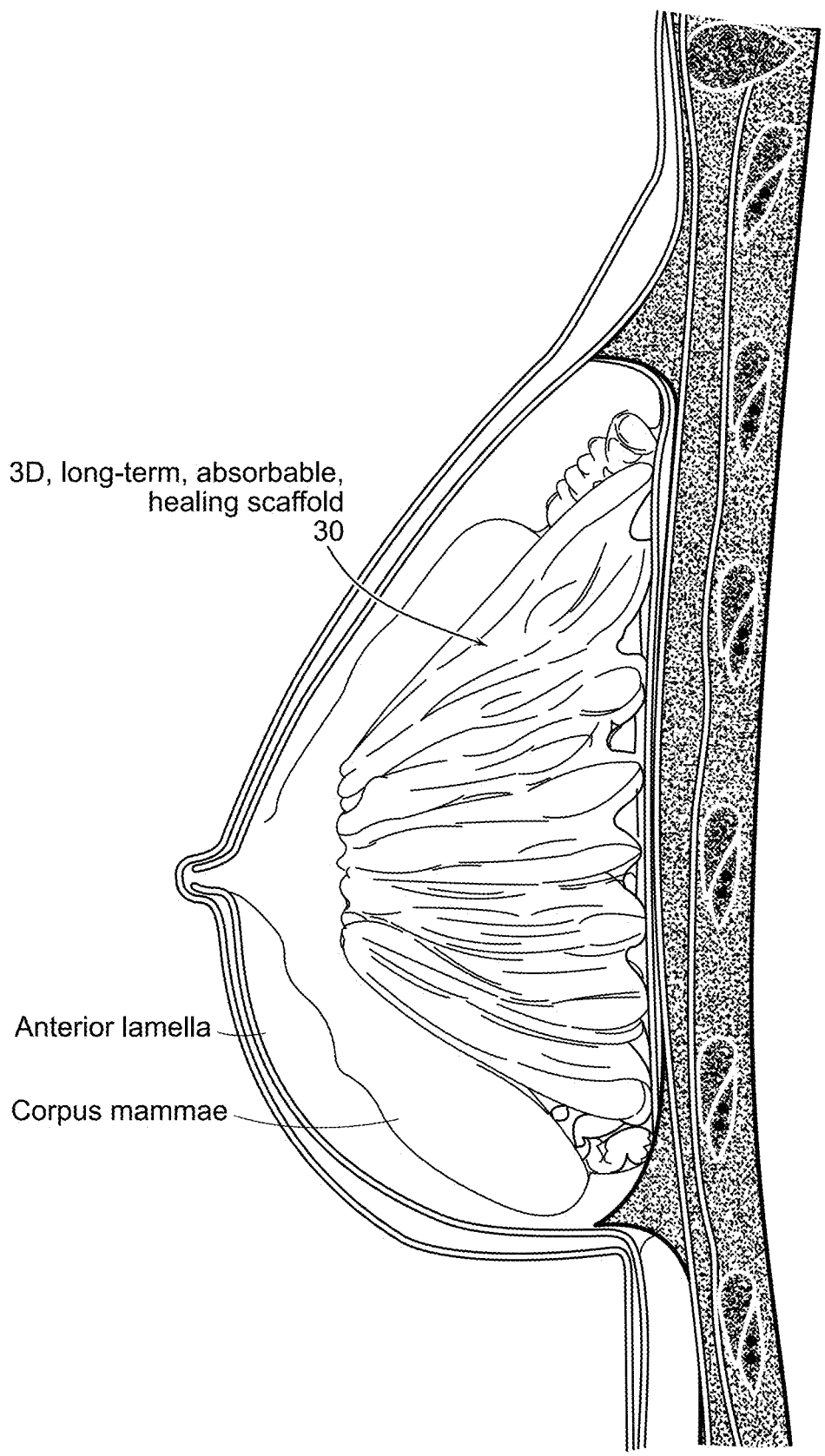
FIG. 8 is a sectional view of a breast with the cup member of the internal brassiere device of the present invention in place and utilizing a long term absorbable scaffold with pleats.

In order to prevent the breast from "rolling downhill" in the recumbent position during sleep, the internal brassiere device of the present invention is utilized. The internal brassiere device can be used when weakening and stretching out of the circum-mammary ligament exists or due to high risk anatomy (like a severe pitch to the slope of the chest wall with weak connective tissue) posing the high chance of sagging after plastic surgery. The ring or first member 22 of the internal brassiere device, of the present invention, is placed into the surgical pocket in the pre-cinched larger diameter shape shown in FIG. 7a, behind the breast gland and on top of the pectoral muscle, then anchored to the surrounding circum-mammary ligament with non-absorbable suture 26. The ring member 22 cinched to the desirable smaller diameter shown in FIG. 7b, thus tightening the circum-mammary ligament and gathering the breast together in higher, more projecting position on the chest (FIG. 8). In breast reconstruction using a skin, nipple, and circum-mammary ligament sparing technique, the cup or second member forming scaffold 30 (FIG. 9) is placed below the anterior lamella fat and in front of the posterior lamella fascia. The cup member 30 adds volume and support to the skin and superficial fascia component of the breast as the patients fibroblast and blood vessels grow into and replace the slowly dissolving long term absorbable matrix. The second member 30 also can serve as a platform for autologous fat transplantation, in situations where breast volume is insufficient and when an implant is not desired.

In the embodiment shown in FIG. 8 the second member 3 is a three-dimensional pleated pyramidal cup structure or member and is anchored with sutures within the ring member 22 of the first member The cup structure is made of very "low weight" or low density knitted fibers and serves a scaffold that autologous fat can be transplanted on to, and for a support of the nipple/breast projection.

Figure 9:
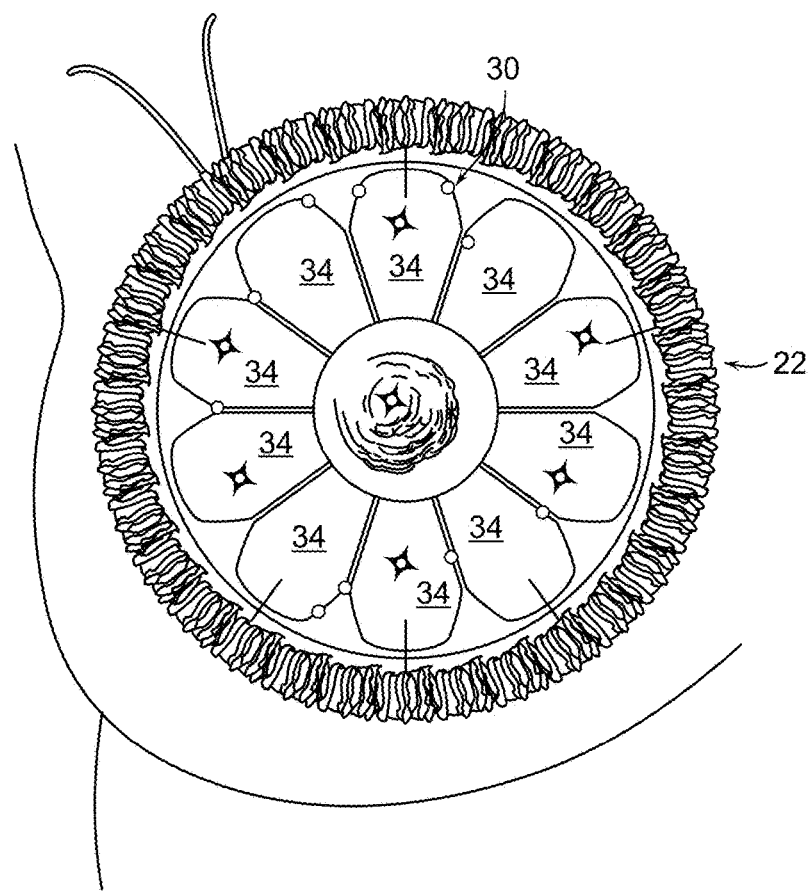
FIG. 9 is a front sectional view of the breast with tree internal brassiere device of present invention shown in FIG. 8.
Figure 10:
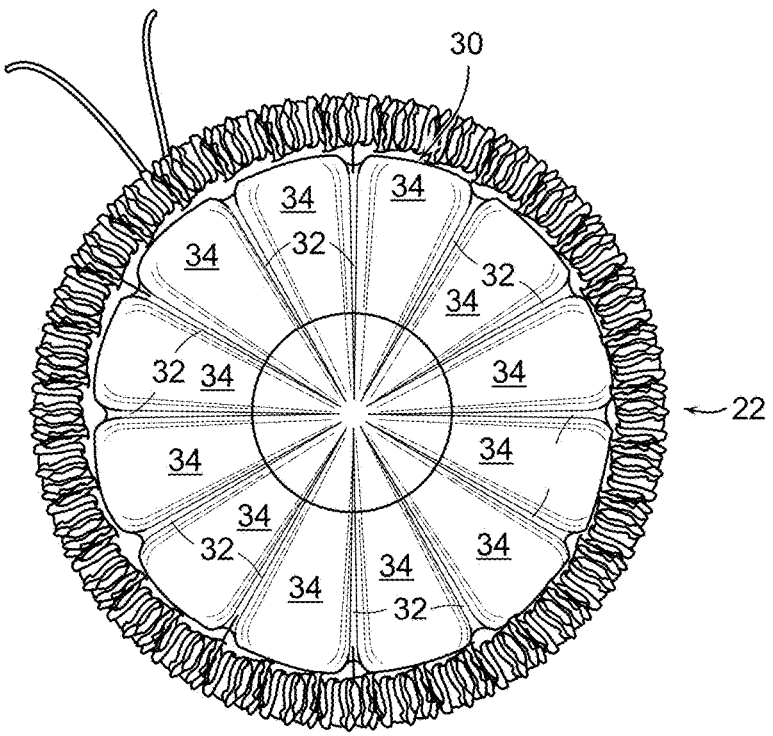
FIG. 10 is a plan view of the internal brassiere device of the present invention shown in FIG. 8.
Figure 11:
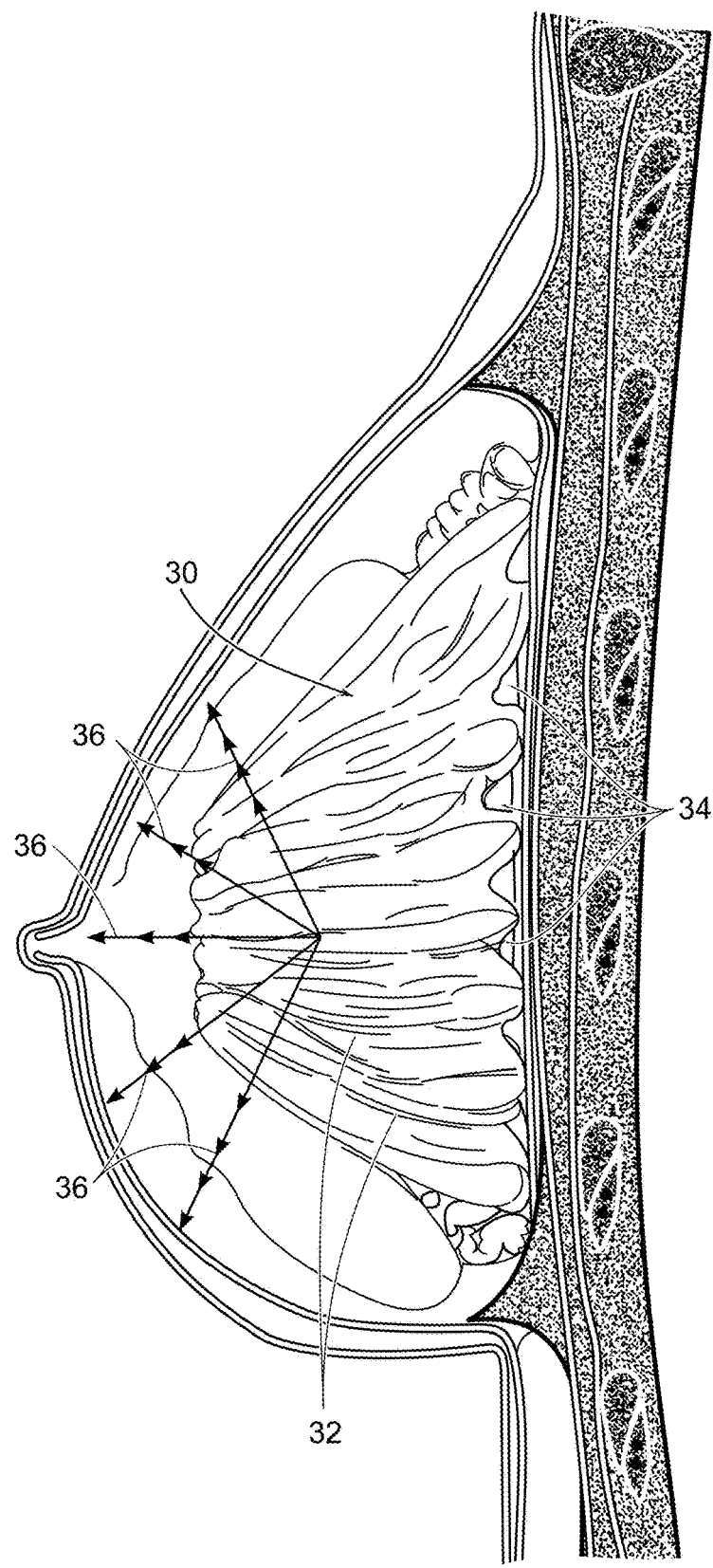
FIG. 11 is a side sectional view of the internal brassiere device of the present invention shown in FIG. 8 with anchoring sutures, formed of twisted twine having unidirectional filaments extending from the cup member within the breast.
Figure 12:
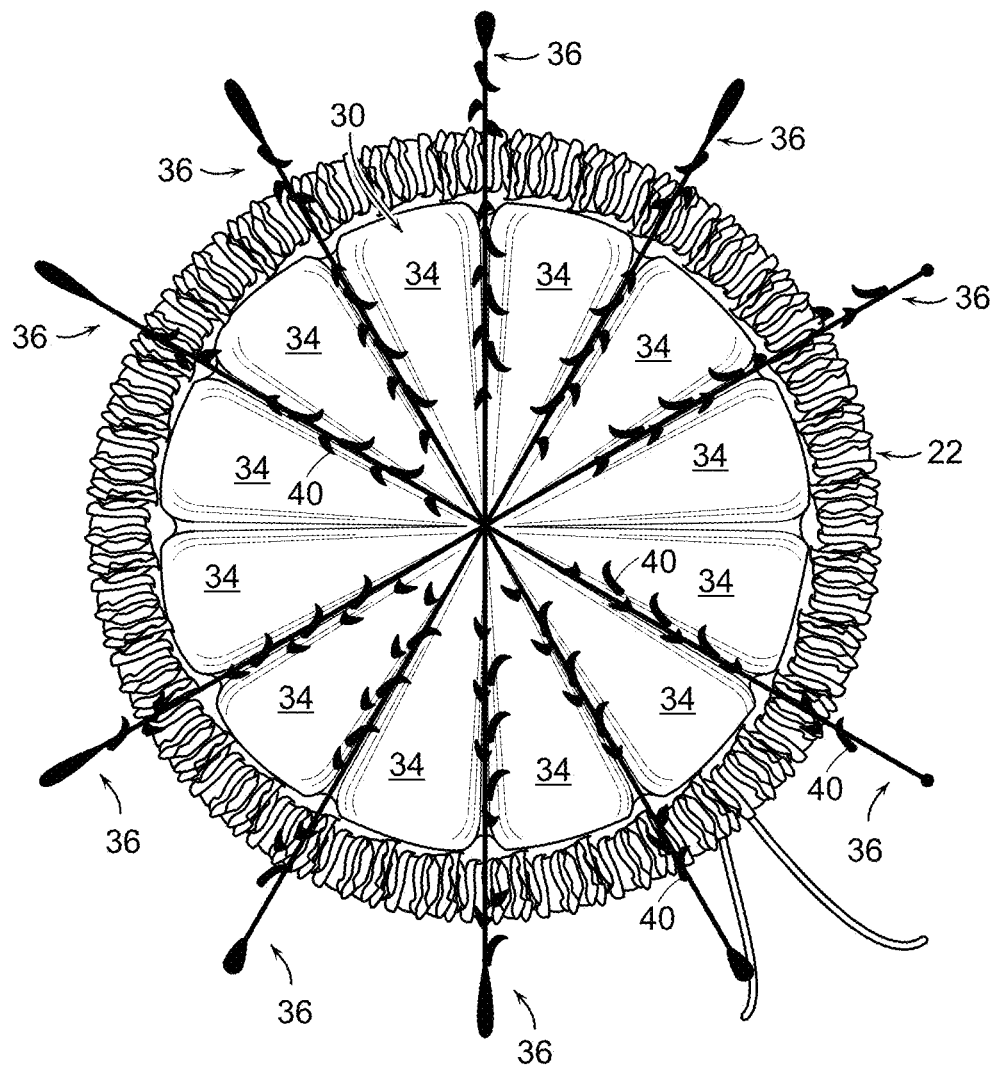
FIG. 12 is a plan view of the internal brassiere device of the present invention with the cup member in the ring member and anchoring sutures extending radially from the central core of the cup member.

FIGS. 9, 10 and 11 show a particularly advantageous cup member according to the present invention wherein the cup member 30 is formed of or more sheets of long term absorbable material which are pleated or folded as shown at 32 to form a plurality of compartments or chambers 34 arranged radially around a central core of he cup member with the cup member having frusto-conical shape. As shown in FIG. 12, a plurality of anchoring sutures 36 radiate from the central core of the frusto-conical cup member and pass through the breast gland to just below the surface of the breast skin to be cut off under tension such that the cut ends recoil below the anterior lamella fascia after cutting and having been inserted with suture passers at the time of the surgical placement of the cup member. The compartments 34 are radially arranged around the central core. The compartments 34 form partially open tissue engineering chambers for the scaffold. Autologous fat grafts be injected over the surface of the compartments prior to insertion of the cup member into the body. Also, tissue regeneration enhancing substances, such as stem cells, growth factors, cytokines, platelets, extracellular and/or adipose matrix proteins are coated onto the matrix surface before inserting into the body. Additionally, the long absorbable matrix material can be coated with anti-cancer substances, such as chemotherapy agents, hormone blocking agents or antibiotics.

Figure 13:
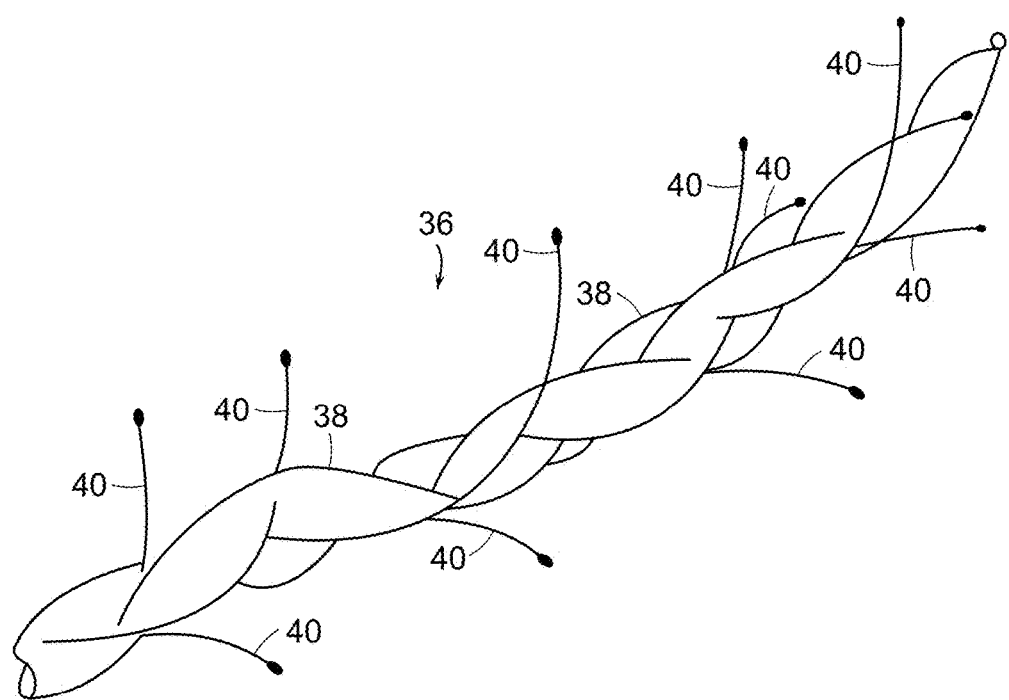
FIG. 13 is a broken perspective view of the anchoring sutures of FIG. 11.
Figure 14:
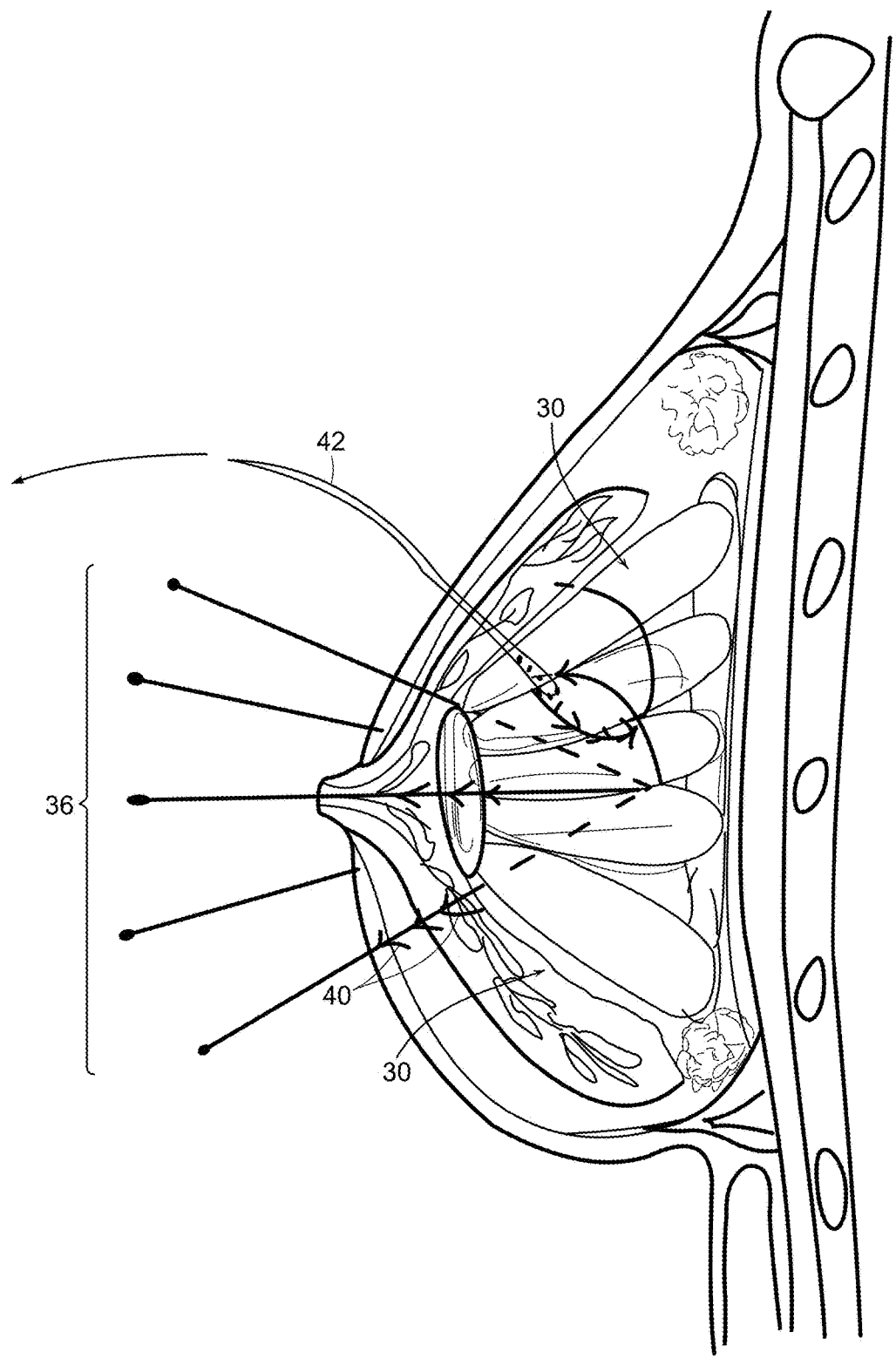
FIG. 14 is a side sectional view of the internal brassiere device of the present invention showing use of a curved suture passer.

The plurality of radially extending anchoring sutures 36 extend from the central core of tie cup member and hold the cup member in place shown in FIGS. 11 and 12. The anchoring sutures can be made of braided twine 38 with unidirectional barbs 40 extending therefrom as shown in FIG. 13 and FIG. 14 wherein a curved suture passer 42 is also shown for use in placing the sutures.

Figure 15:
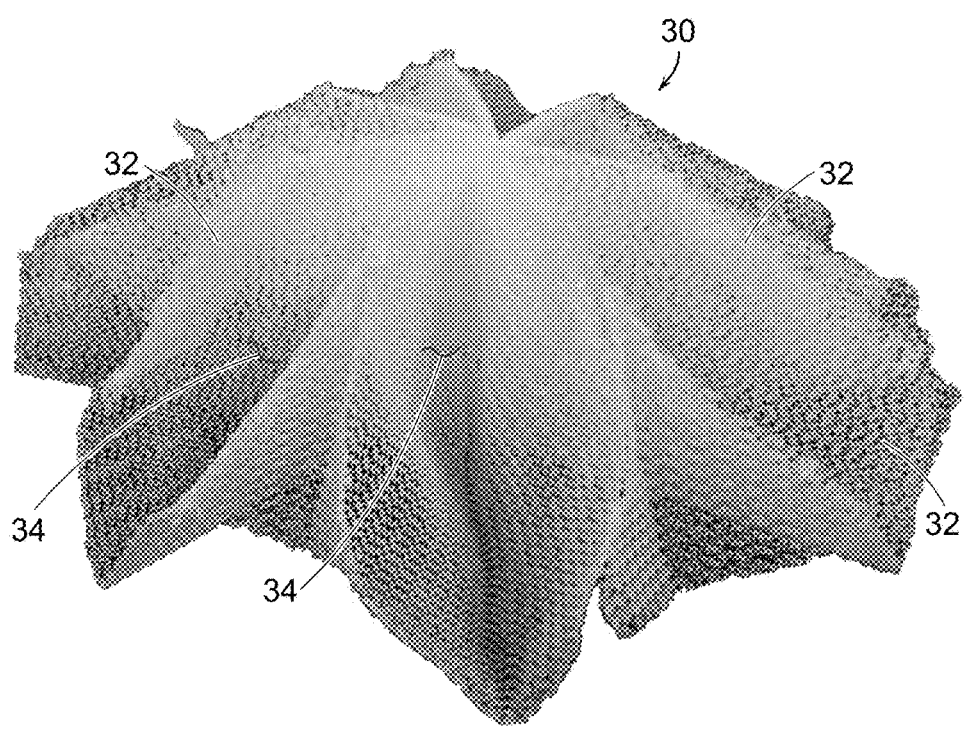
FIG. 15 is a perspective view of the cup member of the internal brassiere device of the present invention showing the plurality of radially arranged compartments formed by the pleated scaffold.

FIG. 15 shows the radial arrangement of the compartments in a perspective view.

The internal brassiere device of the present invention can, thus, be used to treat patients who have undergone a mastectomy, who have undergone breast lift and have a need for augmentation, who have undergone breast reduction and need support and lift of the reduced breast, who have undergone previous silicone implant breast surgery and desire the implant to be removed and subsequent reconstruction of the breast to produce a youthful anatomy, to treat patients who have a youthful breast but desire a fuller breast and larger size and who would, thus, not need the ring member but would benefit from the tissue engineering scaffold to provide projection of the breast away from the chest wall and fat grafted volume added to the breast. Additionally, the internal brassiere device of the present invention permits a mixture of lipoaspirate fatty tissue to be mixed with biologic or synthetic fluidized scaffold matrix for to fill the compartment of the cup member thus holding the micro-globules of liposuctioned fat in place in a three-dimensional, scattered fashion to allow revascularization and prevent pooling of the fat which otherwise could lead to necrosis. Additionally, the compartments can be, prior to insertion in the body, coated with substances known to encourage tissue regeneration and then coated with selected tissue cells such as pancreatic islet cells, hepatic cells, or other cells, and stem cells genetically altered to contain genes for treatment of patient illnesses. The radially arranged compartments provide good neovascularization with mononuclear inflammatory cells and multi-nucleic giant cells as well as adipo-genesis on the matrix surfaces as well as between the layers of folded material. The base of the breast sits on the chest wall which consists of pectoral muscles and the ribcage. The chest wall is wrapped in a sheet of collagen fibers referred to as the deep fascia. As noted above, the superficial fascial system of the breast has a donut-shaped ring of fascia and fat that surrounds the corpus mammae, called the circum-mammary ligament. It fuses to the deep fascia of the chest such that the circum-mammary ligament defines the base diameter of the breast. Two layers of fascia surround the corpus mammae and are integrated with the circum-mammary ligament. Between the corpus and these fascial layers are insulating layers of fat, and the fascia and fat between the skin aid the breast gland are called the anterior lamina and the layer between the corpus and the chest wall is the posterior lamina. Strands or cords of collagen pierce through the breast starting at the posterior lamina fascia and travel through the breast to anchor into the dermis of the overlying skin and are called Cooper's Ligaments. Breast ptosis occurs when the circum-mammary ligament stretches which condition is obviated by the internal brassiere device of the present invention which creates a breast with a small base diameter, high position on the chest and plump fullness that fills the skin. The internal brassiere device of the present invention which the above discussed tensioned fascial elements to establish youthful tension of the system and reinforces the system. Elements of the long term absorbable material (mesh fibers) encourage ingrowth of patient connective tissue and the use of the ring member in combination with the cup member holds the breast in a smaller base diameter and forces the breast volume into more projecting profile (i.e. youthful). The use of a pleated frusto-conical shaped cup member produces a scaffold placed behind the breast gland or, in place of the breast gland, in breast reconstruction following mastectomy, to push the breast up and drat and provide additional volume when liposuctioned fat is grafted onto the cup member to create a perkier fill of the breast skin. As third member or component of the internal brassiere device of the present invention, braided filament with backward oriented strands emanating therefrom, are anchored to the core of the cup her/scaffold and passed from behind the gland through substance of the breast and out of the skin where It is cut under tension while the cutting scissors are used to push down on the skin surface such that the filaments retract below the subcutaneous fat after cutting thereby emulating the function of Cooper's Ligaments.

Some materials that can be used for the long term absorbable matrix (or mesh) include Novus Scientific TIGR mesh, Allergen Seri Surgical Scaffold; Tepha, Inc.'s polymer (Poly-4 Hydroxybutyrate) that is licensed to Bard under the name Phasix, and to Galatea under the name GalaFLEX; Gore long term absorbable mesh called Bio A, and Ethicon Ultrapro. Alternatively, shorter lasting absorbable materials, like polydioxanone could be used in part or whole to allow dissolution of the scaffold in a shorter time frame.

The device of the present invention prevents the breast (and breast implants when present) from pushing down and weakening nature's internal support—the circum-mammary ligament Change in the shape of the breast is due to gradual nightly erosion of the ligament over time, in the same way that orthodontia can move teeth through the jawbone with continuous directional pressure. The slowly absorbable, synthetic internal brassiere device of the present invention, with its members of varying density and thickness, are positioned and assembled during surgery to correct and strengthen the superficial fascia system that defines breast shape—thus constituting an internal long-term absorbable brassiere.

The internal brassiere device of the present invention includes a ring member used for anchoring that can be made in one example, of a knitted tube of material that can compress to a smaller diameter, in an accordion fashion, and used at the periphery of the surgical dissection pocket to function to pull the surgical wound, or pocket, together and help the frusto-conical scaffold cup member maintain a region of low tissue pressure and also defines the region of tissue engineering by anchoring the cup member and holding the surrounding tissue in approximation to the pleated scaffold. The ring member can be made of long term absorbable material or have a percentage of permanent fibers. In the case of breast surgery, the ring member is preferably placed in the anatomic space deep to the breast gland or in a mastectomy defect after the removal of the breast gland and sutured to the fibro-fatty ring of connective tissue surrounding the breast gland that connects to the deep fascia of the circum-mammary ligament. Once the ring member is placed and connected to the circum-mammary ligament, a purse string suture running in and out of the ring member and, the circum-mammary ligament is pulled tight to narrow the base diameter of the breast. The off-loading of tissue pressure within the ring member helps establish an ideal region for tissue regeneration. The cup member formed of a frusto-conical scaffold is made of a long term absorbable mesh material that is folded and pleated into an annular structure to be implanted within the ring member. The cup member tents up the overlying tissue of the surgical wound. The compartments formed in the cup member produce a scaffold having folded chambers arranged around a central core similar to petals of lotus flower. The number of compartments can vary but are normally somewhere between eight and ten thus dividing the greater overall volume of the space for tissue expansion into smaller, subunit spaces. The joining together of the compartments around a central core adds to the stability of the scaffold configuration of the cup member while minimizing the need for mesh material. Extra surface area can be produced by using folded mesh spacers between the compartments. Points of contact between the various folds (pleats) and the ring member can be fastened together using suture, glue, or heat welding of the absorbable mesh material to create a tensegrity system. Tensegrity is a continuous system or network of tension acting on a discontinuous set of compressible elements whose end result is a structure with a floating equilibrium. In the instance of a tissue engineering lotus-like scaffold as in the device of the present invention with multiple points of connection, a tension system and fatty tissue is created which will eventually fill the compartments to create a structure that will bend but not break and return to its original equilibrium shape after distorting influences are removed. Preferably, the long term absorbable mesh material is composed of a loose-knit monofilament such as an absorbable polyester such as Poly-4 Hydroxybutyrate (P4Hb) which is a naturally occurring polymer known to have antibacterial properties and induces M2 phase of inflammation leading to tissue regeneration.

In the situation of a subcutaneous or sub-glandular breast application, the tissue engineering lotus scaffold produced by the cup member is surrounded by the fat and fascia ire the superficial fascia system. Globules of fat and partial globules broken apart by surgical dissection will l into the compartments which is desirable since the collagen matrix of the superficial fascia system with its capillaries and arterials are known to be the location of new adipose tissue creation or adipogenic sites. The large surface area of the scaffold provides structure for neovascularization and three-dimensional locations for distribution of priming substances such as liposuction aspirant. In other priming maneuvers, loose knit, micro porous material of the scaffold can be coated with proteins known to promote tissue regeneration and can be covered with other chemical compounds. The scaffold formed by the cup member can be colonized with undifferentiated stem cell transplants from healthy cells that grow and produce metabolic compounds. The anchoring sutures which are long term absorbable can be equipped with tines or straight needles and run from the scaffold through the overlying breast tissue and out of the skin to anchor in the sub-dermis before being cut thereby maintaining the overlying breast tissue lifted and in the proper relation to the underlying cup member scaffold and chest wall. The anchoring sutures can be braided or twined with several fibers of which a minority percentage can be non-absorbable with a majority percentage being long term absorbable. The interstitial spaces between fibers of the braid or twine are replaced with collagen and fiberglass cells as the sutures are absorbed leaving behind ingrowth of patient tissue resulting in an engineered Cooper's Ligament.

Inasmuch as the present invention is subject to many variations, modifications and changes in detail, it is intended that all subject matter discussed above OF shown in the accompanying drawings be interpreted as illustrative only and not be taken in a limiting sense.

An Internal long absorbable matrix brassiere in ludin ring member adapted to be fixed to the chest of a women and a frusto-conical, pleated scaffold member, fixed within the ring member. A tissue engineering scaffold for implant in the body is formed as a three-dimensional structure composed of one or more pleated sheets of absorbable material and having a plurality of partially open comparments forming tissue engineering chambers for the scaffold.

What is claimed is:

1. An internal, long term absorbable matrix brassiere comprising
   a ring member adapted to be internally fixed to the chest of a woman; and
   a cup member held within said ring member, aid cup member being formed of pleated long term absorbable material forming a scaffold.

2. An internal, long term absorbable matrix brassiere as recited in claim 1 and further comprising a suture disposed within said ring member to be anchored to the circum-mammary ligament, said ring member having a pleated, gathered nature to have a smaller diameter upon being cinched by pulling and tying said suture.

3. An internal, long term absorbable matrix brassiere as recited in claim and further comprising a running suture that courses in and out of said ring member and the circum-mammary ligament to pull said ring member and the circum-mammary ligament into a smaller diameter when said running suture is pulled taut and tied.

4. An internal, long term absorbable matrix brassiere as recited in claim 1 wherein said cup member is made of a three-dimensional matrix, primarily of long term absorbable fibers allowing for arterial and tissue ingrowth.

5. An internal, long term absorbable matrix brassiere as recited in claim 1 wherein said cup member a three-dimensional pleated pyramidal-type structure anchored within said ring member with sutures.

6. An internal long term absorbable matrix brassiere as recited in claim 1 wherein said ring member is a circular tube adapted to be fixed to the circum-mammary ligament of a woman's chest and to receive said cup member.

7. An internal long term absorbable matrix brassiere as recited in claim 1 wherein said cup member is a frusto-conical shaped, pleated structure made of loosely knitted fibers of absorbable matrix.

8. An internal long term absorbable matrix brassiere as recited in claim 1 wherein said cup member is a frusto-conical shaped, pleated structure made of loosely knitted absorbable fibers and loosely knitted fibers of non-absorbable affix.

9. An internal long term absorbable matrix brassiere as recited in claim 1 wherein said cup member is formed of pleated, long term absorbable material forming a surface to which autologous fat can be grafted.

10. An internal long term absorbable matrix brassiere comprising
    a purse-string suture forming a ring member fixed to the circum-mammary ligament by threading, surgically, said purse-string suture through the circum-mammary ligament; and
    a cup member having a base fixed to said ring member and made from sheet material of long term absorbable knitted matrix, said purse-string suture being operable to cinch said ring member and the circum-mammary ligament into a smaller diameter to narrow the base of the breast and create breast projection.

11. An internal long term absorbable matrix brassiere comprising
    a ring member placed in a surgical dissection plane and fixed to the circum-mammary ligament; and
    a cup member having a plurality of compartments arranged around a central core and fixed to said ring member, said cup member having shape made from pleated sheet material of long term absorbable knitted matrix.

12. An internal long term absorbable matrix brassiere as recited in claim 11 wherein the surgical dissection plan is the intra-fascial plane located within the posterior lamina fat and within the posterior lamina fascia.

13. An internal long term absorbable matrix brassiere recited in claim 11 wherein said ring member is made of twisted twine with unidirectional filaments extending in a helical pattern and composed partially of long term absorbable filaments and partially of non-absorbable filaments, said ring member being threaded, surgically, through the circum-mammary ligament and pulled tight and tied, so as to decrease the base diameter of the breast to a desired size.

14. An internal long term absorbable matrix brassiere as recited in claim 11 wherein said ring member is coupled with the circum-mammary ligament using a curved, half round suture passer.

15. An internal long term absorbable matrix brassiere as recited in claim 11 wherein twisted twines, with unidirectional filaments, radiate out from the central core of said frusto-conical cup member, pass through the breast gland to just below the surface of the breast skin and are cut off under tension such that the cut ends recoil below the, anterior lamella fascia after cutting and having been inserted, with suture passers, at the time of surgical placement of said cup member.

16. An internal long term absorbable matrix brassiere as recited in claim 11 wherein said ring member includes a purse-string suture threaded through the circum-mammary ligament and pulled tight to decrease the base diameter of the breast and said cup member is formed of a plurality of compartments radially arranged around a central core and fixed to said ring member, said cup member having a frusto-conical shape and being made from pleated sheets of long term absorbable knitted matrix, said compartments acting as partially open tissue engineering chambers.

17. An internal long term absorbable matrix brassiere as recited in claim 16 wherein autologous fat grafts are injected over the surface of said compartments prior to insertion into the body.

18. An internal long term absorbable matrix brassiere as recited in claim 16 wherein tissue regeneration enhancing substances such as stem cells, growth factors, cytokines, platelets, extracellular adipose matrix proteins, are coated onto the matrix surface before insertion into the body.

19. An internal long term absorbable matrix brassier as recited in claim 16 wherein said matrix coated with anti-cancer substances such as chemotherapy agents, hormone blocking agents, or antibiotics.

20. An internal long term absorbable matrix brassiere as recited in claim 1 wherein said ring member is formed by a suture placed through the circum-mammary ligament for pulling the circum-mammary ligament to a smaller diameter.

21. An internal long term absorbable matrix brassiere as recited in claim 20 wherein said suture is formed by a twine, barbed suture made of part long term absorbable and part non-absorbable twines.

22. An internal long term absorbable matrix brassiere as recited in claim 1 wherein said absorbable material is formed of knitted sheets of mesh material.

23. An internal long term absorbable matrix brassiere as recited in claim 1 wherein said ring member for circular base on the chest if placed on top of the deep fascia of the pectoralis major within the posterior superficial fascia.

24. An internal long term absorbable matrix brassiere comprising a cup member having a plurality of compartments arranged around a central core and fixed to the circum-mammary ligament of the chest of a woman, said cup member having a frusto-conical shape made from pleated sheet material of long term absorbable knitted matrix.

25. A tissue engineering scaffold for implant in the body comprising a three-dimensional structure composed of one or more pleated sheets of absorbable material, said structure having a plurality of partially open compartments forming tissue engineering chambers for said scaffold.

26. A tissue engineering scaffold as recited in claim 25 further comprising autologous fat grafts implanted onto the pleated absorbable material forming said tissue engineering chambers.

27. A tissue engineering scaffold as recited in claim 25 further comprising tissue regeneration enhancing substances coated onto the pleated absorbable material forming said tissue engineering chambers.

28. A tissue engineering scaffold as recited in claim 25 wherein said three-dimensional structure has a central core, said plurality of compartments are arranged radially around said central core and further comprising micro-globules of liposuctioned fat filling said chambers in a three-dimensional scattered fashion allowing revascularization.

29. A tissue engineering scaffold as recited in claim 28 wherein said fat is coated on the surface of said pleated sheets and between layers of said absorbable material formed by folds.

30. A tissue engineering scaffold as recited in claim 25 wherein said three-dimensional structure is annular in shape and said compartments are joined together around a central core stabilizing said three-dimensional structure.

31. A tissue engineering scaffold as recited in claim 25 wherein said absorbable material is mesh and said pleated sheets forming said tissue engineering chambers are fastened together by welding of said absorbable mesh material.

* * * * *

UNITED STATES PATENT AND TRADEMARK OFFICE
CERTIFICATE OF CORRECTION

PATENT NO. : 10,595,986 B2  
APPLICATION NO. : 15/918538  
DATED : March 24, 2020  
INVENTOR(S) : Robert D. Rehnke Page 1 of 1

It is certified that error appears in the above-identified patent and that said Letters Patent is hereby corrected as shown below:

In the Specification

Column 1, Line 57, replace "omen" with --women--.
Column 2, Line 14, replace "istle" with --is the--; Line 36, replace "do" with --on--; Line 58, replace "etching" with --stretching--; Line 67, replace "ere" with --are--.
Column 3, Line 27, replace "a were d" with --grafts were used--; Line 49, replace "b react" with --breast--; Line 62, replace "name" with --mammae is--.
Column 4, Line 44, replace "Il lar" with --acellular--; Line 52, replace "finical" with --clinical--; Line 61, replace "pen-areolar" with --peri-areolar--; Line 62, replace "allows s" with --allows--; Line 64, replace "per-areolar" with --peri-areolar--.
Column 5, Line 35, replace "the breast its" with --the breast to its--; Line 36, replace "as" with --has--; Line 63, replace "n" with --an--.
Column 6, Line 23, replace "suture that runs ,as purse string" with --suture that runs as a purse string--; Line 32, replace "direction" with --direction.--; Line 43, replace "fashion" with --fashion.--; Line 54, replace "ligament and mg member into a member diameter" with --ligament and ring member into a smaller diameter--.
Column 7, Lines 26-28, replace "into its inter tires. Accordingly, the need for a traditional breast plant can be avoided." with --into its interstices. Accordingly, the need for a traditional implant can be avoided.--; Line 61, replace "o breast implant" with --or breast implant--; Line 67, replace "b" with --be--.
Column 8, Line 1, replace "The ring member" with --The ring member is--.
Column 9, Line 20, replace "tree" with --the--.
Column 10, Line 32, replace "3" with --30--; Line 40, replace "of or more" with --of one or more--.
Column 12, Line 1, replace "drat" with --out--; Line 7, replace "her scaffold" with --member/scaffold--; Line 25, replace "ligament" with --ligament.--.

Signed and Sealed this  
Second Day of June, 2020

Andrei Iancu  
*Director of the United States Patent and Trademark Office*